(12) United States Patent
Ye

(10) Patent No.: US 11,020,419 B2
(45) Date of Patent: Jun. 1, 2021

(54) USE OF POLYINOSINIC-POLYCYTIDYLIC ACID COMPOSITIONS IN TREATMENT OF MALIGNANT EFFUSION

(71) Applicant: BIOSYNGEN PTE, LTD, Singapore (SG)

(72) Inventor: Sheng Ye, Guangdong (CN)

(73) Assignee: BIOSYNGEN PTE, LTD, Singapore (SG)

( * ) Notice: Subject to any disclaimer, the term of this patent is extended or adjusted under 35 U.S.C. 154(b) by 15 days.

(21) Appl. No.: 16/463,275

(22) PCT Filed: Sep. 26, 2017

(86) PCT No.: PCT/CN2017/103511
§ 371 (c)(1),
(2) Date: May 22, 2019

(87) PCT Pub. No.: WO2018/059404
PCT Pub. Date: Apr. 5, 2018

(65) Prior Publication Data
US 2019/0328767 A1 Oct. 31, 2019

(30) Foreign Application Priority Data

Sep. 30, 2016 (CN) .......................... 201610881917.6

(51) Int. Cl.
| | | |
|---|---|---|
| *C07H 21/04* | (2006.01) | |
| *A61K 31/713* | (2006.01) | |
| *A61P 35/04* | (2006.01) | |
| *A61K 33/14* | (2006.01) | |
| *A61K 39/00* | (2006.01) | |
| *A61K 39/12* | (2006.01) | |
| *A61K 47/36* | (2006.01) | |
| *C07H 21/02* | (2006.01) | |

(52) U.S. Cl.
CPC .......... *A61K 31/713* (2013.01); *A61K 33/14* (2013.01); *A61K 39/0011* (2013.01); *A61K 39/12* (2013.01); *A61K 47/36* (2013.01); *A61P 35/04* (2018.01); *C07H 21/02* (2013.01)

(58) Field of Classification Search
CPC .................................................. C12N 15/113
See application file for complete search history.

(56) References Cited

FOREIGN PATENT DOCUMENTS

| CN | 101590227 A | 12/2009 |
|---|---|---|
| CN | 102488707 A | 6/2012 |
| CN | 103599071 A | 2/2014 |
| CN | 104434784 A | 3/2015 |
| WO | 2008/048560 A1 † | 4/2008 |
| WO | 2008133595 A1 | 11/2008 |
| WO | 2013/083659 A1 † | 6/2013 |
| WO | 2017/171653 A1 † | 10/2017 |

OTHER PUBLICATIONS

International Search Report PCT/PCT/CN2017/103511, dated Jan. 9, 2018.
Anthony VB, et al., "Management of Malignant Pleural Effusions", Eur Respir J 2001; 18: pp. 402-419.
Mark E. Roberts, et al., "Management of a Malignant Pleural Effusion: British Thoracic Society Pleural disease Guideline 2010", Thorax2010 65: ii32-ii32-ii40, doi: 10.1136/thx.2010.
Barni S., et al., A Novel Perspective for an Orphan Problem: Old and New Drugs for the Medical Management of Malignant Ascites, doi:10.1016/j.critrevonc.2010.07.016, pp. 144-153.
Dawei Chen, et al., "Sustained Response of Malignant Pericardial Effusion to Intrapericardial Bevacizummab In an Advanced Lung Cancer Patient: A Case Report and Literature Review" Onco Targets and Therapy Oct. 1, 2015: 8 pp. 2767-2770.
Kaifi JT, et al., "Multidisciplinary Management of Malignant Pleural Effusion", Journal of Surgical Oncology 2012; 105: pp. 731-738.
Lila Ammouri, et al., "Palliative Treatment of Malignant Ascites: Profile of Catumaxomab", Biologics: Targets & Therapy May 7, 2010: 4 pp. 103-110.
Magda Spella, et al., "Switching Off Malignant Pleural Effusion Formation—Fantasy Or Future?", Journal of Thoracic Disease, vol. 7, No. 6 Jun. 2015, pp. 1009-1020.
Michael Ried, et al., "The Treatment of Pleural Carcinosis With Malignant Pleural Effusion", Deutsches Ärzteblatt International | Dtsch Arztebl Int 2013; 110(18): 313-8.
Muhammad W. Saif, et al., "Management of Ascites Due to Gastrointesetinal Malignancy", Ann Saudi Med 2009; 29 (5): pp. 369-377.
Olopade, Olufunmilayo, et al., "Malignant Effusions" vol. 41, No. 3 May/Jun. 1991, pp. 166-179.
Schulze M. et al., "Effective Treatment of Malignant Pleural Effusion by Minimal Invasive Thoracic Surgery: Thoracoscopic Tale Pleurodesis and Pleuroperitoneal Shunts in 101 Patients",Ann Thorac Surg 2001;71:1809 -12.
Stathopoulos GT, et al., "Malignant Pleural Effusion: Tumor-Host Interactions Unleashed", Am J Respir Crit Care Med. Author manuscript; available in PMC Oct. 20, 2017.
Warren WH, et al., "Identification of Clinical Factors Predicting Pleur Catheter Removal in Patients Treated for Malignant Pleural Effusion" , European Journal of Cardio-thoracic Surgery 33 (2008) 89-94.
Ma, B. et al. RIG-like Helicase Regulation of Chitnase 3-like-1 Axis and Pulmonary Metastasis. Sci. Rep. 6, 26299; doi: 10.1038/srep26299 (May 2016).†

* cited by examiner

*Primary Examiner* — Kimberly Chong
(74) *Attorney, Agent, or Firm* — Lerner, David, Littenberg, Krumholz & Mentlik, LLP

(57) ABSTRACT

The use of an immunomodulating composition comprising polyinosinic:polycytidylic acid (PIC) in the treatment or prevention of malignant effusion, or the alleviation of symptoms of malignant effusion. The composition may further comprise a stabilizer and/or calcium ion, anti-cancer agent, an antigen or any pharmaceutically acceptable carriers.

12 Claims, 7 Drawing Sheets

USE OF POLYINOSINIC-POLYCYTIDYLIC ACID COMPOSITIONS IN TREATMENT OF MALIGNANT EFFUSION

CROSS-REFERENCE TO RELATED APPLICATIONS

The present application is a national phase entry under 35 U.S.C. § 371 of International Application No. PCT/CN2017/103511 filed Sep. 26, 2017, which claims priority from Chinese Patent Application No. 201610881917.6, filed Sep. 30, 2016, all of which are hereby incorporated by reference.

FIELD OF THE INVENTION

The present invention relates to the use of an immunomodulating composition comprising polyinosinic:polycytidylic acid (PIC) in the treatment or prevention of malignant effusion, or the alleviation of symptoms of malignant effusion. The composition may further comprise a stabilizer and calcium ion, anti-cancer agent, an antigen or any pharmaceutically acceptable carriers.

BACKGROUND

Malignant pleural effusion (MPE) is generally defined by the presence of malignant cells in the pleural fluid or pleural tissue. It is very common among patients with malignant tumors at later stage of disease [Kaifi J T, et al., *Journal Surg Oncol* 2012; 105: 731-8]. Common symptoms associated with MPE are dyspnea, cough, fatigue, weight loss and pleuritic pain.

A classic view of MPE formation is due to pleural fluid retention resulting from lymphatic obstruction of tumor development in pleural space. These pleural-based tumor metastases block pleural fluid drainage, while increasing pleural fluid production via enhanced plasma extravasation into the pleural space. It is now believed that MPE results from a complex biological interplay between the host vasculature and tumor cells, involving the mediators of the host immune system [Stathopoulos G T, et al., *Am J Respir Crit Care Med* 2012; 186:487-92].

The frequency of MPE is about 500 new cases per million population per year. It is predominantly found with adenocarcinomas of the lungs and other organs, signaling incurability, shortened life expectancy, and severely compromised quality of life [Light R W, et al., *Textbook of pleural diseases*. Philadelphia: Lippincott, Williams and Wilkins; 2001. 4; Antunes G, et al., *Thorax* 2003; 58: ii29-ii38]. The prognosis of patients with MPE is very limited, with a mean survival of approximately 6 to 8 months. In addition to limited survival, patients also suffer significantly reduced quality of life, with frequent medical interventions usually as a result of recurring pleural effusions [Antunes G, et al., *Thorax* 2003; 58: ii29-ii38]. Therefore, the primary aim of treatment for patients with pleural carcinosis is usually palliative care in the form of a reduction in clinical complaints [Neragi-Miandoab S, *Lung Cancer* 2006; 54: 1-9].

Because of the lungs' close anatomical proximity to the pleurae, MPE is seen in about 8-15% of lung cancer patients, accounting for approximately 40% of all MPE cases. The second-most common cause is metastatic breast cancer (accounting for approximately 25% of MPE), followed by lymphoma (approximately 10%), ovarian cancer (approximately 5%), and gastro-intestinal cancers (approximately 5%) [Michael Ried, et al., *Dtsch Arztebl Int* 2013; 110(18); Antony V B, et al., *Eur Respir J* 2001; 18: 402-19; Putnam J B, *Surg Clin North Am* 2002; 82: 867-83. 7-9].

Similarly, malignant ascites (MA) and pericardial effusion (MPCE) are defined as a condition in which excessive fluid containing cancerous cells accumulates in the peritoneal or pericardial cavities. The potential causes of ascites include peritoneal carcinomatosis that obstructs lymphatic draining, portal vein thrombosis, congestive heart failure, constrictive pericarditis, nephrotic syndrome and peritoneal infections [Muhammad W. Saif, et al., *Ann Saudi Med.* 2009 September-October; 29(5): 369-377]. The cancers most commonly associated to MA are ovarian (37%), pancreato-biliary (21%), gastric (18%), oesophageal (4%), colorectal (4%), and breast (3%) [Barni S, et al., *Critical Reviews in Oncology/Hematology* 2011; 79: 144-153].

As an acute and repeatedly occurring event, a chest drain is usually recommended for immediate relief of MPE, followed by other treatments options that are also mostly invasive, such as temporary or permanent pleural catheter insertion, and thoracoscopic pleurodesis. Systemic chemotherapy is another available option for patients whose primary tumor is still chemo-sensitive. Simultaneous radiotherapy may further improve survival for such patients [Magda Spella, et al., *J Thorac Dis* 2015; 7(6):1009-1020].

Most systemic cytotoxic drug has been tested in small trials via local perfusion route with different degree of success. These include cisplatin, melphalan, 5-fluorouracil, carboplatin, mytomycin C, etoposide, doxorubicin, paclitaxel, mitoxantrone, cytarabine, topotecan, and methotrexate, either alone or in combination. However, with the development of MPE, the underlying tumor has become chemoresistant in most cases, and many patients are not fit for further chemotherapy.

Current treatment options for MPCE and MA are similar as MPE. For MPCE, the first choice is usually local therapy, such as pericardial intraluminal stenting or fenestrated drainage. Pericardial perfusion of antitumor drugs is common, but the effectiveness of such strategies is limited [Lila Ammouri, et al., *Biologics* 2010; 4: 103-110]. Available therapies for MA palliation also include the use of diuretics, implantation of drainage catheters, and surgical shunting techniques [Dawei Chen, et al. *OncoTargets and Therapy* 2015]. However, none of these palliation options affect the course of disease.

Despite recent progress in cancer treatment, malignant effusion remains a dismal event and is associated with high morbidity and mortality. Current therapeutic approaches are medically demanding, inefficient, and often, unable to address the underlining causes.

Immunotherapy has recently emerged as a potent therapeutic option for cancer treatment. It has been shown to generate a tumor suppression effect in a number of major cancer types. Two newly approved PD-1 antibodies Nivolumab (Opdivo) and Pembrolizumab (Keytruda) were approved in NSCLC and chemo-refractory melanoma respectively.

Here, the inventor used a potent immunomodulating composition, comprising polyinosinic:polycytidylic acid (PIC), aiming at reinventing the host immune response and restoring the disfunctioning host immune system against cancer. The inventor surprisingly found that such composition was effective in relieving malignant effusion.

DETAILED DESCRIPTION

Figure 1:
FIG. 1 shows body weight of mice post cancer cell inoculation (D) and treatment.

The present invention may be understood more readily by reference to the following detailed description of certain embodiments of the invention and the Examples included herein.

Unless defined otherwise, all technical and scientific terms used herein have the same meaning as commonly understood by one of ordinary skilled in the art to which this invention belongs. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a polyinosic:polycytidylic acid composition" includes a plurality of such compositions.

Composition and Medical Use

The present invention concerns a composition comprising polyinosinic:polycytidylic acid (PIC) for use in a method of treatment of malignant effusion. The composition may further comprise stabilising agent (s). The composition may be an immunomodulating composition.

In one aspect of the present invention a composition comprising a polyinosinic:polycytidylic acid (PIC) is provided for use in a method of treatment of malignant effusion.

In another aspect of the present invention the use of a polyinosinic:polycytidylic acid (PIC) in the manufacture of a medicament for use in the treatment of malignant effusion is provided.

In another aspect of the present invention a method of treatment of malignant effusion is provided, the method comprising administering to a subject in need of a composition comprising a polyinosinic:polycytidylic acid (PIC).

PIC is typically a double stranded polymer comprising one strand of inosinic acid polymer (polyinosinic acid; polyI) and one strand of cytidylic acid polymer (polycytidylic acid; polyC). The polymer backbone may be a deoxyribonucleic acid backbone or ribonucleic acid backbone. The PIC may be an oligonucleotide analog. In a preferred embodiment, the polyI is preferably polyriboinosinic acid. In a preferred embodiment, the PIC is preferably polyribocytidylic acid. In preferred embodiments the PIC is polyriboinosinic:polyribocytidylic acid, i.e. a double stranded RNA (dsRNA)-like polymer.

The composition may comprise at least one stabilising agent. In a particular embodiment, the composition comprises: polyinosinic:polycytidylic acid (PIC), and at least one stabilising agent, wherein the amount of PIC is about 0.1 to 10.0 g/L.

In some embodiments, the ratio between the anionic charge of the PIC and cationic charge of the stabilising agent is 0.1:1, 0.2:1, 0.3:1, 0.4:1, 0.5:1, 0.6:1, 0.7:1, 0.8:1, 0.9:1, 1:1, 1:1.1, 1:1.2, 1:1.3, 1:1.4, 1:1.5, 1:1.6, 1:1.7, 1:1.8, 1:1.9, or 1:2.0, preferably the ratio is 1:1.

The composition may comprise calcium ions. The composition may comprise calcium chloride ($CaCl_2$)), which may provide a source of calcium ions.

In some embodiments, the stabilizing agent is an aminoglycoside or non-aminoglycoside amine. An aminoglycoside is any organic molecule that contains an amino-sugar substructure. Traditionally, a group of bacterial derivatives also called aminoglycosides are used as medicinal and therapeutic agents to inhibit protein synthesis of Gram-negative bacteria. In some particular embodiments, an aminoglycoside antibiotic is selected from the group consisting of Dihydrostreptomycin, Mannosidostreptomycin, Amikacin, Butyrosin, Dibekacin, Destomycin, Gentamicin, Kanamycin, Lividomycin, Netilmicin, Neomycin, Paromomycin, Ribostamycin, Sisomicin, Streptomycin, Streptothricin, Tobramycin and Validamycin. In a preferred embodiment, the aminoglycoside is Kanamycin.

In one aspect of the present invention a composition comprising a polyinosinic:polycytidylic acid (PIC); Kanamycin; and calcium chloride ($CaCl_2$), for use in a method of treatment of malignant effusion is provided. The PIC is preferably a polyriboinosinic:polyribocytidylic acid.

In some embodiments, the amount of PIC in the composition described above is about 0.1 to 10.0 g/L, 0.2 to 8.0 g/L, 0.5 to 6.0 g/L, 0.6 to 5.0 g/L, 0.8 to 3.0 g/L, 1.0 to 2.0 g/L.

In some embodiments, the amount of kanamycin in the composition described above is about 100 to 5000 IU; 300 to 3000 IU, 500 to 2000 IU, 600 to 1500 IU per 1.0 mg of kanamycin.

In some embodiments, the amount of calcium chloride in the composition described above is about 0.02 to 10.0 mmol/L, 0.05 to 8.0 mmol/L, 0.1 to 5.0 mmol/L, 0.2 to 4.0 mmol/L, 0.5 to 3.0 mmol/L, or 0.8 to 2.0 mmol/L.

In some embodiments, the composition is administered by parenteral administration, intramuscular injection, intraperitoneal perfusion, intrapleural perfusion, intravenous perfusion, subcutaneous injection, intrapericardial injection, inhalation, endorectal perfusion, suppository, intra nasal, ophthalmic, transdermal or oral administration.

In some embodiments in accordance with various aspects of the present invention, the malignant effusion is located in the pleural, peritoneal, and/or pericardial cavity; and the malignant effusion arises from a primary tumor originating in the lung, lymph, liver, stomach, colon, breast, ovary, pancreas, biliary duct, esophagus, brain, nose or prostate gland.

In some embodiments, the malignant effusion is located in the pleural, peritoneal, and/or pericardial cavity; and the malignant effusion arises from metastases of tumor originated from the lung, lymph, liver, stomach, colon, breast, ovary, pancreas, biliary duct, esophagus, brain, nose or prostate gland.

In a particular embodiment, the malignant effusion is located in the pleural cavity and arises from metastases of the lung cancer, lymphoma, stomach cancer, colon cancer, breast cancer or ovary cancer.

In another embodiment, the malignant effusion is located in the peritoneal cavity and arises for metastases of the ovary cancer, pancreatic cancer, biliary duct cancer, or esophagus cancer.

In a particular embodiment, the composition comprises: a polyriboinosinic:polyribocytidylic acid (PIC); a stabilizing agent; and calcium chloride ($CaCl_2$). wherein, a) the amount of PIC is about 0.1 to 10.0 g/L; and/or b) the amount of stabilizing agent is about 1.0-10.0 g/L; and/or c) the amount of calcium chloride is about 0.2 to 4.0 mmol/L.

In a more particular embodiment, the composition comprises: a polyriboinosinic:polyribocytidylic acid (PIC); kanamycin; and calcium chloride ($CaCl_2$), wherein, a) the amount of PIC is 0.1 to 10.0 g/L; and/or b) the amount of kanamycin is 100 to 5000 IU per 1.0 mg of PIC; and/or c) the amount of calcium chloride is 0.02 to 10.0 mmol/L.

In an even more particular embodiment, the composition comprises: a polyriboinosinic:polyribocytidylic acid (PIC); kanamycin; and calcium chloride ($CaCl_2$), wherein, a) the amount of PIC is 0.5 to 6.0 g/L; and/or b) the amount of kanamycin is 500 to 2000 IU per 1.0 mg of PIC; and/or c) the amount of calcium chloride is 0.2 to 4.0 mmol/L.

Formulation

Compositions according to the present invention may preferably be formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, A. Gennaro (2000) "Remington: The Science and Practice of Pharmacy," 20* edition, Lippincott, Williams, & Wilkins; Pharmaceutical Dosage Forms and Drug Delivery Systems (1999) N. C. Ansel et al., eds., 7t ed., Lippincott, Williams, & Wilkins; and Handbook of Pharmaceutical Excipients (2000) A. H. Kibbe et al., eds., 3rd ed. Amer. Pharmaceutical Assoc.

The PIC composition with or without other pharmaceutically acceptable ingredients may be prepared in a solid or liquid form. In particular, the composition can be in the form of a liquid solution, liquid drops, liquid suspensions, emulsions, sprays, inhalants, aerosols, syrups, slurries, enemas. In some related embodiments, the composition is in the form of solid capsules, soft capsules, suppository, microcapsules, tablets, coated tablets, dragees, granules, powders, tablets or lozenges.

For parenteral administration in an aqueous solution, for example, the solution should be suitably buffered if necessary and the liquid diluent first rendered isotonic with sufficient saline or glucose. These particular aqueous solutions are especially suitable for intravenous and intraperitoneal administration. In this connection, sterile aqueous media, which can be employed, will be known to those of skill in the art in light of the present disclosure. Exemplary injection media, which can be used in the present invention, include a buffer with or without dispersing agents and/or preservatives, and edible oil, mineral oil, cod liver oil, squalene, mono-, di- or triglyceride, and a mixture thereof.

The exact amount of such compositions required will vary from subject to subject, depending on the species, age, weight, and general conditions of the subject, the severity of the disease, infection, or condition that is being treated or prevented, the particular compound used, its mode administration, and the like. An appropriate amount may be determined by one of ordinary skill in the art using only routine experimentation given the teachings herein. Following an initial administration, subjects may receive one or several booster immunizations adequately spaced.

When the composition is formulated for local administration, the formulation may allow the composition to stay at the site of administration for a prolonged period of time, thus providing a depot of composition that will give sustained release or pulsatile release in vivo. Such a delivery system may allow administrations that would otherwise require multiple applications to elicit an antidote effect.

In some embodiments, the composition further comprises an anticancer agent. The anticancer agent may be a chemotherapy drug or anticancer monoclonal antibody. In other embodiments, the composition may be used as an adjuvant therapy before, together or after the administration of a chemotherapy drug or anticancer monoclonal antibody.

Kit

In another aspect, a kit comprising a therapeutically or prophylactically effective amount of a composition or pharmaceutical composition described herein is provided. The kit may further comprise instructions, e.g. written instructions or a computer readable medium containing instructions, for the use of the composition in the treatment of malignant effusion.

In some embodiments, the invention is packaged in a kit comprising a sterile liquid (e.g., aqueous) formulation, where the formulation is sterile, and is provided in a sterile container, a sterile vial, or a sterile syringe and optionally a needle. In some embodiments, the invention is packaged in a kit comprises the antidote composition in a sterile liquid formulation in a unit dosage amount (e.g., a single dose).

In certain embodiments, the kit further comprises a delivery system suitable for intrapleural perfusion, intraperitoneal perfusion, intrapericardial perfusion, intravenous infusion or subcutaneous injection. The kit in some embodiments will further include instructions for use, including e.g., dosage amounts and dosage frequencies. Instructions are in some embodiments printed directly on the kit. In other embodiments, instructions are printed material provided as a package insert. Instructions can also be provided in other media, e.g., electronically in digital or analog form, e.g., on an audio cassette, an audio tape, a compact disc, a digital versatile disk, and the like.

Methods

Methods according to the present invention may comprise treating, preventing or alleviating the symptoms of malignant effusion, and may comprise administering to a subject a therapeutically or prophylactically effective amount of the composition or pharmaceutical composition. The method may further comprise a pre-treatment and/or post-treatment, e.g. with chemotherapy, radiotherapy or other standard of care treatment.

The composition may be administered during a chest drainage, thoracentesis, temporary or permanent pleural catheter insertion, thoracoscopic pleurodesis, pericardial intraluminal stenting or fenestrated drainage, or surgical shunting procedure. This may optionally be part of co-treatment or adjuvant therapy. In some embodiments, the composition is administered via intrapleural perfusion, intraperitoneal perfusion, intrapericardial perfusion, intravenous infusion or subcutaneous injection.

Administration of compositions according to the present invention is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

By way of example, suitable dosage amounts may include about 0.1 to 10.0 g/L PIC, or 100 ug to about 10,000 ug/ml PIC, e.g. one of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3200, 3400, 3600, 3800, 4000, 4200, 4400, 4600, 4800, 5000, 5500, 6000, 6500, 7000, 7500, 8000, 8500, 9000, 9500, 10,000 ug PIC. Unit doses of PIC may be in the range about 100 ug to about 500 ug PIC, about 500 ug to about 1000 ug PIC, about 1000 ug to about 1500 ug PIC, about 1500 ug to about 2000 ug PIC, about 2000 ug to about 2500 ug PIC, about 2500 ug to about 3000 ug PIC, about 3000 ug to about 3500 ug PIC, about 3500 ug to about 4000 ug PIC, about 4000 ug to about 4500 ug PIC, about 4500 ug to about 5000 ug PIC, about 5000 ug to about 5500 ug PIC, about 5500 ug to about 6000 ug PIC, about 6000 ug to about 6500 ug PIC, about 6500 ug to about 7000 ug PIC, about 7000 ug to about 6500 ug PIC, about 7500 ug to about 8000 ug PIC, about 8000 ug to about 8500 ug PIC, about 8500 ug to about 9000 ug PIC, about 9000 ug to about 9500 ug PIC, or about 9500 ug to about 10,000 ug PIC.

A subject may receive a single dose of a composition according to the present invention. More preferably a subject will receive more than one dose, and may receive one of at least 2, 3, 4, 5, 6, 7, 8, 9, 10 or more doses. Each dose may be a unit dose. Doses may be administered according to a program of treatment and may be administered at regular intervals, e.g. once or twice daily, once, twice, three, four, five or six times per week, once every two, three, four, five or six days, once fortnightly, or once, twice, three, four, five or six times every month.

The subject to be treated may be at risk of developing malignant effusion. The composition may modulate the immune response of the subject to prevent, reduce or alleviate malignant effusion.

Several mediators are associated with malignant effusion, including tumor secreted vasoactive mediator, VEGF; tumor oncogenetic transformation mediator, EGFR and Kras gene overexertion. Study has shown both tumor and host cells secrete inflammatory mediators, such as CCL2 and SPP1, TNF-alpha, IL-6, and IL-27 that promote the formation of malignant effusion. Tumor cells also interact with host immune response to increase vascular permeability. This is partly achieved by over-expression of TNF-alpha, which also activates the NF-kB pathway to regulate cell survival.

In some embodiments, the effect of administering the composition of the present invention to a subject, determined to have malignant effusion, is to modulate the immune response of the subject and can be quantified by one or more of the following parameters:

a) an increase VEGF expression in malignant fluid or serum;

b) an increase IFN-γ in malignant fluid or serum;

c) a decrease TNF-alpha in malignant fluid or serum;

d) a decrease peritoneal permeability;

and one or more of (a), (b), (c) or (d) (in any combination) may be respectively increased or decreased by one of at least 10%, at least 20%, at least 30%, at least 50%, at least 80%, at least 100% (2-fold), at least 3-fold, at least 5-fold or more.

Medical Target

In this specification, a cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells.

In preferred embodiments, a cancer is one that is associated with effusion fluid. Such association may involve production of effusion fluid by the cancerous tissue, e.g. by cancer cells, or by normal cells near to or contained in the cancerous tissue, or it may involve overproduction of effusion fluid by other tissues (e.g. the lymphatic system) as a direct or indirect response to the presence of the cancer in the subject.

A cancer may be characterised by the collection of effusion fluid in one or more locations in the subject's body. Such locations may include one or more body cavities or tissue spaces. Body cavities (or serous cavities) may be formed by a serous membrane surrounding an organ or tissue and forming a sac in which fluid may collect.

For example, effusion fluid may collect in one or each (right or left) pleural cavity (the space between the visceral and parietal pleura). In another example, effusion fluid may accumulate in the peritoneal cavity (the space between the parietal peritoneum and visceral peritoneum). In another example, fluid may accumulate in the pericardial cavity surrounding the heart (formed by the parietal and visceral pericardium). In another example, fluid may accumulate in the perimetrium surrounding the uterus.

Thus, in some embodiments a cancer is one in which pleural effusion, peritoneal effusion (ascites), pericardial effusion or perimetrial effusion occurs.

All types of cancer may be associated with production of effusion fluid, partly because all types of cancer can metastasize to any of the body's serous cavities and result in malignant effusion [Olopade O I and Ultmann J E, *CA: A Cancer Journal for Clinicians* 1991; Vol. 41, No. 3; 166-179]. Cancers in which production of effusion fluid is known to occur include cancers of at least the following type or tissues: lung cancers, pleural cancers, mesothelioma, malignant pleural mesothelioma, non-small cell lung cancer (NSCLC), small cell lung cancer (SCLC), ovarian cancers, ovarian carcinoma, uterine cancer, endometrial cancer, heart cancer, breast cancer, colon cancer, stomach cancer, gastric cancer, pancreatic cancer, kidney cancer, liver cancer, lymphatic cancer (e.g. lymphoma, non-Hodgkin lymphoma), soft tissue sarcoma, osteosarcoma, adenocarcinoma, parotid cancer (e.g. parotid adenocarcinoma), thymic carcinoma, cancers of the reproductive tract (including cervical, fallopian tube, endometrium), gastrointestinal tract, or genitourinary tract, leukemia, larynx, prostate, bile duct, hypernephroma, sinus piriformis carcinoma, thyroid cancer, melanoma and cancers of unknown primary (CUP) origin.

The development of a malignant pleural effusion is a common complication of advanced malignancies of many types of cancer, especially breast, lung (including NSCLC and SCLC) and ovarian carcinoma [Warren W H, et al., *European Journal of Cardio-thoracic Surgery* 2008; 33: 89-94]. Pleural effusions are at least known to be associated with cancers of the following type or tissue: lung, breast, lymphoma, uterus, ovarian, female reproductive tract (e.g. cervical, fallopian tube, endometrium), leukemia, pancreas, kidney, colon, stomach (gastric), mesothelioma, sarcoma, larynx, prostate, bile duct, hypernephroma, sinus piriformis carcinoma, thyroid cancer, non-Hodgkin lymphoma, malignant melanoma, reproductive tract, gastrointestinal tract, genitourinary tract, [Warren W H, et al., Management of malignant pleural effusions using the Pleur(x) catheter. *Ann Thorac Surg* 2008; 85:1049-55; Warren W H, et al., *European Journal of Cardio-thoracic Surgery* 2008; 33: 89-94; Schulze M, et al., *Ann Thorac Surg* 2001; 71: 1809-12; Olopade O I and Ultmann J E, *CA: A Cancer Journal for Clinicians* 1991; Vol. 41, No. 3; 166-179].

Peritoneal effusions (ascites) are at least known to be associated with cancers of the following type or tissue: ovarian, epithelial related ovarian, uterus, breast, colon, gastric, pancreatic, hepatic, colon, lymphoma, mesothelioma, and cancers of unknown primary (CUP) origin [Olopade O I and Ultmann J E, *CA: A Cancer Journal for Clinicians* 1991; Vol. 41, No. 3; 166-179].

Pericardial effusions are at least known to be associated with cancers of the following type or tissue: lung, breast, leukemia, lymphoma, sarcoma, melanoma [Olopade O I and Ultmann J E, *CA: A Cancer Journal for Clinicians* 1991; Vol. 41, No. 3; 166-179].

Effusion fluid refers to an excess of fluid produced by a subject in direct or indirect response to the presence of a cancer in the subject. In preferred embodiments the effusion fluid collects in a body cavity such that accumulation of effusion fluid may occur where the rate of production of the effusion fluid exceeds the rate of reabsorption. Pleural effusions (sometimes called malignant pleural effusions) lead to accumulation of fluid in the pleural cavity and occur in some lung cancers, e.g. mesothelioma. Effusion fluid collecting in the peritoneal cavity is commonly referred to as ascites, and can be a symptom of a number of types of cancer including cancer of the breast, lung, colon, stomach, pancreas, ovary, endometrium as well as lymphoma. Pericardial effusion is the abnormal accumulation of fluid in the pericardial cavity. The effusion fluid is preferably exudative.

Effusion fluid can be drained from a respective body cavity by well-known aseptic procedures (e.g. see Warren W H, et al., *European Journal of Cardio-thoracic Surgery* 2008; 33: 89-94; Warren W H, et al., *Ann Thorac Surg* 2008; 85:1049-55).

In some instances, a tube or catheter is inserted in the body cavity in order to drain effusion fluid. Drainage of effusion fluid is a common part of the diagnosis, treatment and management of many forms of cancer. Drainage of effusion fluid provides a means of obtaining a sample of a subject's effusion fluid for diagnostic analysis.

In this specification treatment of malignant effusion may refer to the prevention of build-up of effusion fluid, reduction of amount of effusion fluid and/or alleviation of symptoms associated with the build-up of effusion fluid. The malignant effusion is preferably associated with a cancer, e.g. as described above. The treatment may also optionally treat, reduce or prevent progression of, reduce or prevent metastasis of, or shrink, the associated cancer.

Subject for Treatment

The subject to be treated may be any animal or human. The subject is preferably mammalian, more preferably human. The subject may be a non-human mammal, but is more preferably human. The subject may be male or female. The subject may be a patient. A subject may have been diagnosed with a cancer, or be suspected of having a cancer prior to diagnosis. The subject may exhibit a malignant effusion or be at risk of developing a malignant effusion, e.g. one of pleural effusion, peritoneal effusion (ascites) or pericardial effusion.

In accordance with the present invention PIC molecules may be used to treat subjects having malignant effusion. The PIC molecules may be of any length, and may have any molecular weight.

High Molecular Weight PIC

In some embodiments PIC molecules may have a high molecular weight of at least 30 kDa. In some embodiments, PIC molecules have a minimum molecular weight of one of at least 33 kDa, at least 40 kDa, at least 45 kDa, at least 50 kDa, at least 60 kDa, at least 66 kDa, at least 80 kDa, at least 90 kDa, at least 100 kDa, at least 110 kDa, at least 120 kDa, at least 132 kDa, at least 140 kDa, at least 150 kDa, at least 165 kDa, at least 170 kDa, at least 180 kDa, at least 190 kDa, at least 200 kDa, at least 231 kDa, at least 264 kDa, at least 297 kDa, or at least 330 kDa. The PIC molecules may have a maximum molecular weight of 500,000 kDa or 1,000,000 kDa.

High molecular weight PIC molecules may have 50 base pairs or more. In some embodiments the high molecular weight PIC molecules may have one of 50 base pairs or more, 55 base pairs or more, 60 base pairs or more, 65 base pairs or more, 70 base pairs or more, 75 base pairs or more, 80 base pairs or more, 85 base pairs or more, 90 base pairs or more, 95 base pairs or more, 100 base pairs or more, 110 base pairs or more, 120 base pairs or more, 130 base pairs or more, 140 base pairs or more, 150 base pairs or more, 160 base pairs or more, 170 base pairs or more, 180 base pairs or more, 190 base pairs or more, 200 base pairs or more, 250 base pairs or more, 300 base pairs or more, 350 base pairs or more, 400 base pairs or more, 450 base pairs or more, or 500 base pairs or more. The PIC may have a maximum of 5000 or 10,000 base pairs.

Low Molecular Weight PIC

In some embodiments PIC molecules may have a low molecular weight of 30 kDa or less. In some embodiments, PIC molecules have a maximum molecular weight of one of 30 kDa or less, 25 kDa or less, 20 kDa or less, 18 kDa or less, 16 kDa or less, 15 kDa or less, 14 kDa or less, 13 kDa or less, 12 kDa or less, 11 kDa or less, 10 kDa or less, 9 kDa or less, 8 kDa or less, 7 kDa or less, 6 kDa or less, 5 kDa or less, 4 kDa or less, 3 kDa or less, 2 kDa or less. The PIC molecules may have a minimum molecular weight of 1 kDa or 0.5 kDa.

Low molecular weight PIC molecules may have 50 base pairs or less. In some embodiments the low molecular weight PIC molecules may have 45 base pairs or less, 40 base pairs or less, 35 base pairs or less, 30 base pairs or less, 25 base pairs or less, 20 base pairs or less, 15 base pairs or less, 10 base pairs or less, 5 base pairs or less, or 3 base pairs or less. The PIC may have a minimum of at least 2 base pairs.

In some embodiments, PIC is preferably synthetic and is preferably obtained by de novo chemical synthesis. Synthetic PIC molecules may be obtained from commercial suppliers (e.g. Sigma, or Midland Certified). PIC molecules may be synthesised with or chemically modified to contain 2'-position modifications such as 2'O-methyl, 2'-Fluoro or 2'-$NH_2$.

In some embodiments, PIC compositions is obtained by mixing the polyinosinic and polycytidylic acid in a certain ratio. Preferably, the ratio may be 0.5:1.0, 0.6:1.0, 0.7:1.0, 0.8:1.0, 0.9:1.0, 1.0:1.0, 1.0:1.1, 1.0:1.2, 1.0:1.3, 1.0:1.4, 1.0:1.5, 1.5:1.0, 1.4:1.0, 1.3:1.0, 1.2:1.0, 1.1:1.0, 1.0:0.9, 1.0:0.8, 1.0:0.7, 1.0:0.6, or 1.0:0.5. In a preferred embodiment, the ratio is 1:1. Moreover, the mixture is further mixed with 200 to 2000 IU of kanamycin, and 0.02 to 10 mM $CaCl_2$).

In a particularly useful embodiment, PIC compositions may contain PIC molecules that are heterogeneous in size. In some embodiments, it is preferred that the average (e.g. mean) molecular weight of PIC molecules in the composition is of a selected molecular weight or number of base pairs, as described above. In other embodiment s, it is preferred that at least 60% of the PIC molecules in the composition have a selected molecular weight or number of base pairs. More preferably, this is one of at least 65%, 70%, 75%, 80%, 85%, 90%, 95%, 96%, 97%, 98%, 99% or 100%.

In some embodiments PIC may be formulated into a pharmaceutical composition or medicament for use in treatment, preferably treatment of a malignant effusion or cancer. Pharmaceutical compositions and medicaments may comprise a therapeutically effective amount of PIC with a pharmaceutically acceptable carrier, medium, excipient or diluent.

Medicaments and pharmaceutical compositions may be formulated for administration by a number of routes, including but not limited to, parenteral, intravenous, intra-arterial, intramuscular, intratumoral, intrapleural, intraperitoneal, intrapericardial, subcutaneous, oral and nasal. The medicaments and compositions may be formulated in fluid or solid form. Fluid formulations may be formulated for administration by injection to a selected region of the human or animal body.

EXAMPLES

The above disclosure generally describes the present invention. The following example will be of assistance to the understanding of the present invention. These examples are described solely for purposes of illustration and are not intended to limit the scope of the invention.

Example 1

Pharmaceutical Preparation of a PIC, Kanamycin and $CaCl_2$) (BSG) Composition

Mix polyinosinic acid and polycytidylic acid in a ratio from between 0.5 to 1.5 to between 1.5 to 0.5. Add 200 to 2000 IU kanamycin sulfate and 0.02 to 10 mM $CaCl_2$) to the mixture. Top up the volume using PBS and stir the mixture under 60 degrees Celsius for 30 to 60 minutes. Filter the mixture and fill into 2 ml bottle. Some particular preparation is tabulated below:

TABLE 1

| Preparations | PI | PC | Kanamycin (IU/mg) | $CaCl_2$ (mM/L) | Final Volume |
|---|---|---|---|---|---|
| Preparation 1 | 0.5 | 1.5 | 500 | 0.02 | 10 L |
| Preparation 2 | 0.5 | 1.5 | 1000 | 0.02 | 10 L |
| Preparation 3 | 0.5 | 1.5 | 1500 | 0.02 | 10 L |
| Preparation 4 | 1.5 | 0.5 | 500 | 0.02 | 10 L |
| Preparation 5 | 1.5 | 0.5 | 1000 | 0.02 | 10 L |
| Preparation 6 | 1.5 | 0.5 | 1500 | 0.02 | 10 L |
| Preparation 7 | 1.0 | 1.0 | 1000 | 0.8 | 20 L |
| Preparation 8 | 1.0 | 1.0 | 1000 | 5.0 | 20 L |
| Preparation 9 | 0.8 | 1.0 | 1000 | 0.5 | 10 L |
| Preparation 10 | 1.2 | 1.0 | 1000 | 0.5 | 10 L |
| Preparation 11 | 1.0 | 0.8 | 1000 | 0.5 | 10 L |
| Preparation 12 | 1.0 | 1.2 | 1000 | 0.5 | 10 L |

Example 2

Use of BSG in Preventing and Controlling MA in Animal Model

MA is common manifestation in digestive system neoplasms and ovarian cancer, both metastasis via the blood and lymph system. The cancer cells can be implanted to form celiac metastasis as a result of surgical procedure or tumor development process, which leads to excessive accumulation of fluid in the peritoneal cavity. The following experiment will discuss the effect of above mentioned pharmaceutical preparation in controlling MA.

Materials: mice liver cancer cell line H22; female mice 6-8 weeks old, 18-22 g. BSG, containing 2 mg/ml PIC, produced in-house; comparator, DDP purchased from Jiangzu Haoseng; negative control normal saline (N.S).

Methods: Thaw H22 cell line, wash before inject intraperitoneally (i.p.) into 2 female BALB/c mice, and wait 10 days for peritoneal fluid accumulation. Draw accumulated fluid on D10, adjust the cell density at $1 \times 10^7$/ml. Inject another 54 mice via i.p. route with 0.2 ml of the fluid containing total of $2 \times 10^6$ cancerous cells. Pick 18 mice and divide into 2 groups at random 24 h post-inoculation. Each group of mice receives either A. BSG (subcutaneous, s.c. 200 ug/ul) or B. DDP (intraperitoneal, i.p. 20 ug/ul) at dosage set out below as a preventive measure. Treat mice daily for 14 days. The rest of mice were divided into 4 groups at random 5 d post-inoculation, namely C. BSG group (s.c.), D. BSG group (i.p.), E. DDP group (i.p.), and F. control group (s.c., N.S). Treat mice daily for 10 days (grouping detail see table below).

TABLE 2

| Group | No. Animal | Treatment | Daily Dose | Daily Dose (vol.) | Appl. Route |
|---|---|---|---|---|---|
| A | 9 | BSG preventive | 200 ug | 100 ul | s.c |
| B | 9 | DDP preventive | 20 ug | 100 ul | i.p |
| C | 9 | BSG | 200 ug | 100 ul | s.c |
| D | 9 | BSG | 200 ug | 100 ul | i.p |
| E | 9 | DDP | 20 ug | 100 ul | i.p |
| F | 9 | N.S | 0 | 100 ul | s.c |

Observations: 1) record mice behavior and skin/fur glossiness daily; 2) measure body weights and abdomen circumference every two days, record survival status; 3) at D15 (2 d post-treatment), pick 3 mice with largest abdominal circumference from each group, obtain blood from eye venous plexus and separate serum; after obtaining blood, execute mice by cervical dislocation, measure ascites volume; 4) record survival status of the rest of mice, calculate average increase in life span (ILS) using formula=[(ave. survival days of treatment groups/ave. survival days of control group)−1]×100%; 5) calculate rate of MA suppression (%)= (1−ave. MA volume of treatment groups/ave. MA volume of control group)×100%.

Results:

1) All mice behaved normally while alive, skin/fur glossiness was in accordance with animal healthiness. Mice in Group A and C showed highest level of activity. At the 7th day post inoculation, only one animal in Group A had one small size nodule at left abdominal; 6 mice in Group B had medium size nodules while all animals showed reduced activities; one mice in Group C developed one small size nodule; 2 mice in Group D developed medium size nodules; 6 mice in Group E developed medium size nodules and two animals showed reduced activity since D11, increasing in nodule size is observed on D14, all mice in Group F developed medium size nodules and only one survived until D13. It is obvious that BSG groups, namely Group A and C, showed better efficacy in controlling tumor implantation compare to DDP groups and control.

2) In General, mice in DDP groups (both preventive and treatment groups) experienced weight loss after dosing with body weight keep going down. As a result, the average body weight of mice in DDP groups are the lowest among experimental groups on D15, reflecting the excessive toxicity DDP exerted towards tested animals. On the other hand, the higher than average body weight of control group was caused by cancerous growth and excessive fluid accumulation (see FIG. 1).

Figure 2A:
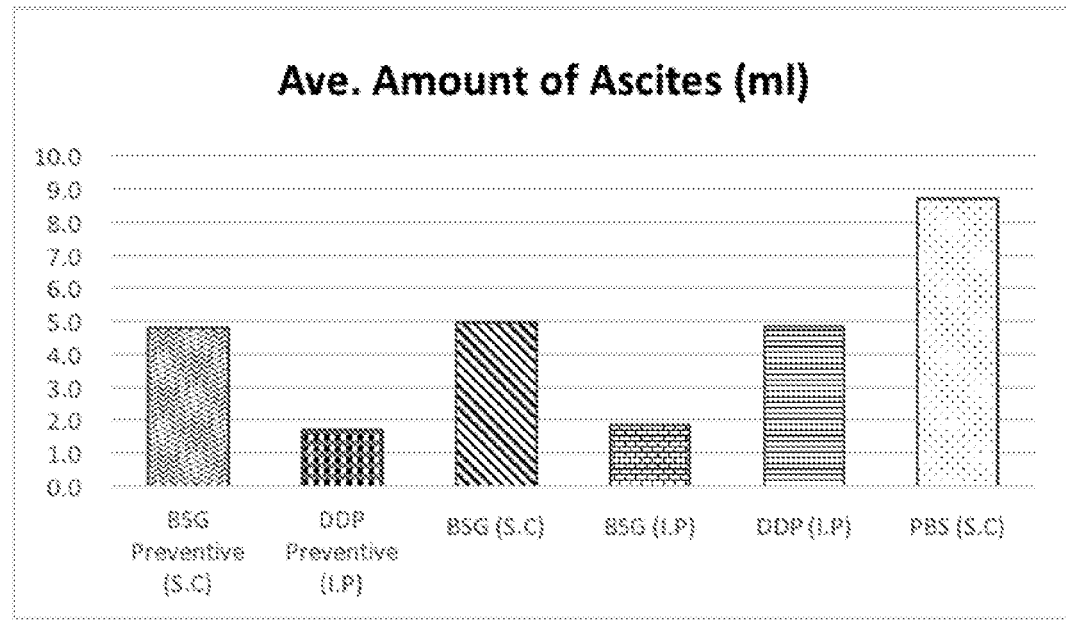
FIG. 2a shows average ascites volume (ml) on D15.

3) For ascites control, animals receiving i.p. administration of BSG and DDP was on par for ascites volume (on average 1.8 ml and 1.7 ml respectively) while BSG was less toxic. According to cell count 2D post-treatment, the average cancerous cells in ascites for each experimental group were 2.42, 3.17, 1.43, 0.97, and 4.85. The data for Group E was missing due to excessive death (details see FIG. 2a).

4) All animals in Group A survival until D15 before executed for testing, while the number of mice survived till D15 in other groups are 6, 7, 5, 2 and 0 for Groups B, C, D, E, F respectively (see table 3). ILS and standard deviation (SD) for each treatment group was calculated and tabulated below:

TABLE 3

| Group | No. mice survive through Day 15 | Ave. survival (days) | SD | SE | ILS |
|---|---|---|---|---|---|
| A. BSG (S.C) Preventive | 9 | 15.0 | 0.0 | 0.0 | 79% |
| B. DDP (I.P) Preventive | 6 | 14.4 | 1.0 | 0.4 | 72% |
| C. BSG (S.C) | 7 | 14.2 | 1.6 | 0.7 | 70% |
| D. BSG (I.P) | 5 | 13.8 | 1.7 | 0.7 | 65% |
| E. DDP (I.P) | 2 | 12.8 | 1.8 | 0.8 | 53% |
| F. PBS (S.C) | 0 | 8.4 | 1.6 | 0.6 | 0% |

Figure 2B:
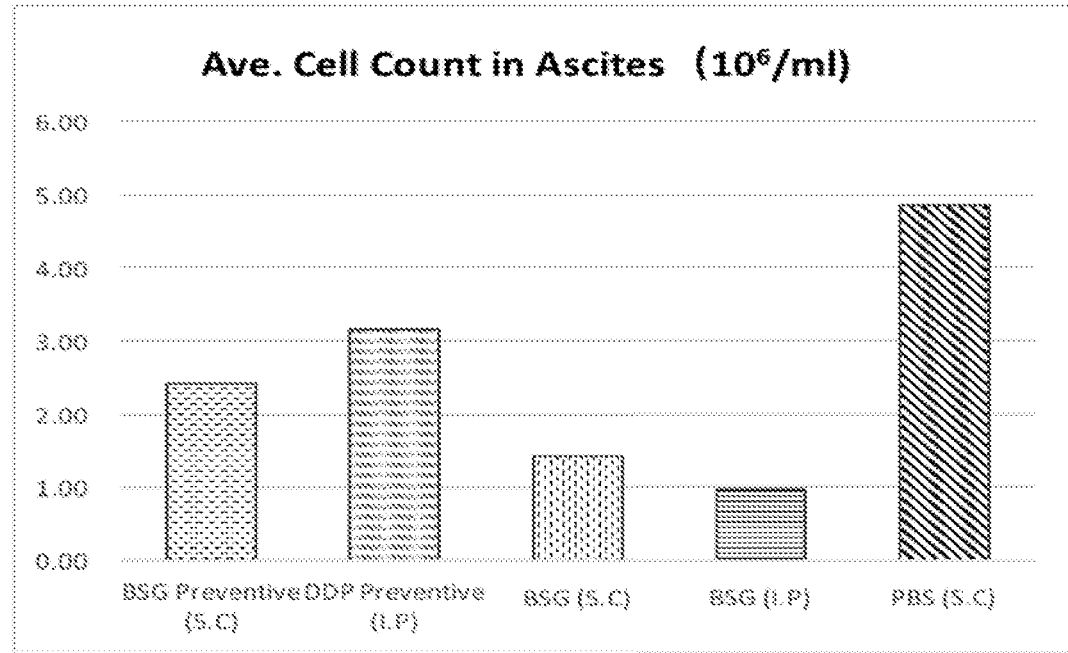
FIG. 2b shows average number of cancerous cells in ascites ($10^6$/ml).

5) In terms of rate of ascites control, Group D receiving BSG i.p. treatment showed best rate of control about 55.2% on D15 (not shown). Interestingly, BSG given both via s.c. and i.p. route in the delayed treatment groups produced a lower cancerous cell count in ascites (see FIG. 2b).

As a conclusion, BSG has superior efficacy over DDP in prolonging animal survival and controlling ascites formation. Combine with the tumor implantation observation, the s.c. route seemed to give better systemic effect in controlling tumorous growth and survival, while i.p. route was more effective in controlling ascites volume.

Example 3

Use of BSG in Controlling and Treating MPE in Mice:

MPE usually refers to tumors originated from the chest metastasis to the pleural space, which leads to the formation of excessive fluid containing cancerous cells and it accounts for about 50% of all pleural effusions. We discuss here the effectiveness of the claimed composition in controlling and treating MPE in comparison to existing chemotherapeutic drugs, as well as synergetic effect produced by drug combination. Materials: mice liver cancer cell line line (purchased from CCTCC), BAL/c mice (female, 6-7 weeks old, 18-22 g, SPF, purchased from Wei Tong Li Hua, Beijing). BSG, 2 mg/ml, produced in house. Comparator CTX (cyclophosphamide, 0.2 g, from Baxter Oncology GmbH, batch no. 6D111A). Sodium Chloride for Injection (2.25 g, 250 ml, 0.9%, from Zhejiang Tianrui, pharmaceutica, batch no. 116102506).

Methods: Thaw H22 cells, adjust density to $1 \times 10^7$ cells/ml, then inject 3 mice, 0.2 ml each. Collect excessive fluid from the injected mice on after 7 days and adjust cell density to $5 \times 10^5$/ml, inject another 78 mice into the peritoneal muscle, 0.2 ml/mouse. Divided the mice randomly into 6 groups of 14 mice each three days post-inoculation, among the 14 mice of each group, 6 will be kept separately for survival study (see Table 4b). Treat mice continuously (grouping detail see Table 4a and 4b).

TABLE 4a

| | | Drug 1 | | | Drug 2 | | | | |
|---|---|---|---|---|---|---|---|---|---|
| Group | Name | Dosage (mg/kg) | Volume (ul/mouse) | Appl. Route | Name | Dosage (mg/kg) | Volume (ul/mouse) | Appl. Route | No. of Mice |
| A1 | BSG | 7.5 | 100 | I.M | — | — | — | — | 8 |
| B1 | CTX | 30 | 100 | I.M | — | — | — | — | 8 |
| C1 | BSG | 7.5 | 100 | I.M | CTX | 30 | 100 | I.M | 8 |
| D1 | BSG | 3 | 100 | I.M | — | — | — | — | 8 |
| E1 | BSG | 0.6 | 100 | I.M | — | — | — | — | 8 |
| F1 | N.S | 0 | 0 | I.M | — | — | — | — | 8 |

TABLE 4b

| | | Drug 1 | | | Drug 2 | | | | |
|---|---|---|---|---|---|---|---|---|---|
| Group | Name | Dosage (mg/kg) | Volume (ul/mouse) | Appl. Route | Name | Dosage (mg/kg) | Volume (ul/mouse) | Appl. Route | No. of Mice |
| A2 | BSG | 7.5 | 100 | I.M | — | — | — | — | 6 |
| B2 | CTX | 30 | 100 | I.M | — | — | — | — | 6 |
| C2 | BSG | 7.5 | 100 | I.M | CTX | 30 | 100 | I.M | 6 |
| D2 | BSG | 0.6 | 100 | I.M | — | — | — | — | 6 |
| E2 | N.S | 0 | 0 | I.M | — | — | — | — | 6 |

Observations: 1) record mice behavior and skin/fur glossiness daily, measure body weights every two days; 2) 5 h post-treatment on D6, obtain blood from eye venous plexus until death and separate serum for white blood cell count (at least 20 ul); after obtaining blood, execute mice by cervical dislocation, measure pleural fluid volume and obtain thymus, spleen and lung, record organ weight; 3) record survival status of the rest of mice in Groups A2 to E2, calculate average increase in life span (ILS) using formula=[(ave. survival days of treatment groups/ave. survival days of control group)−1]×100%; 4) calculate rate of MPE suppression (%)=(1−ave. MPE volume of treatment groups/ave. MPE volume of control group)×100%.

Figure 3:
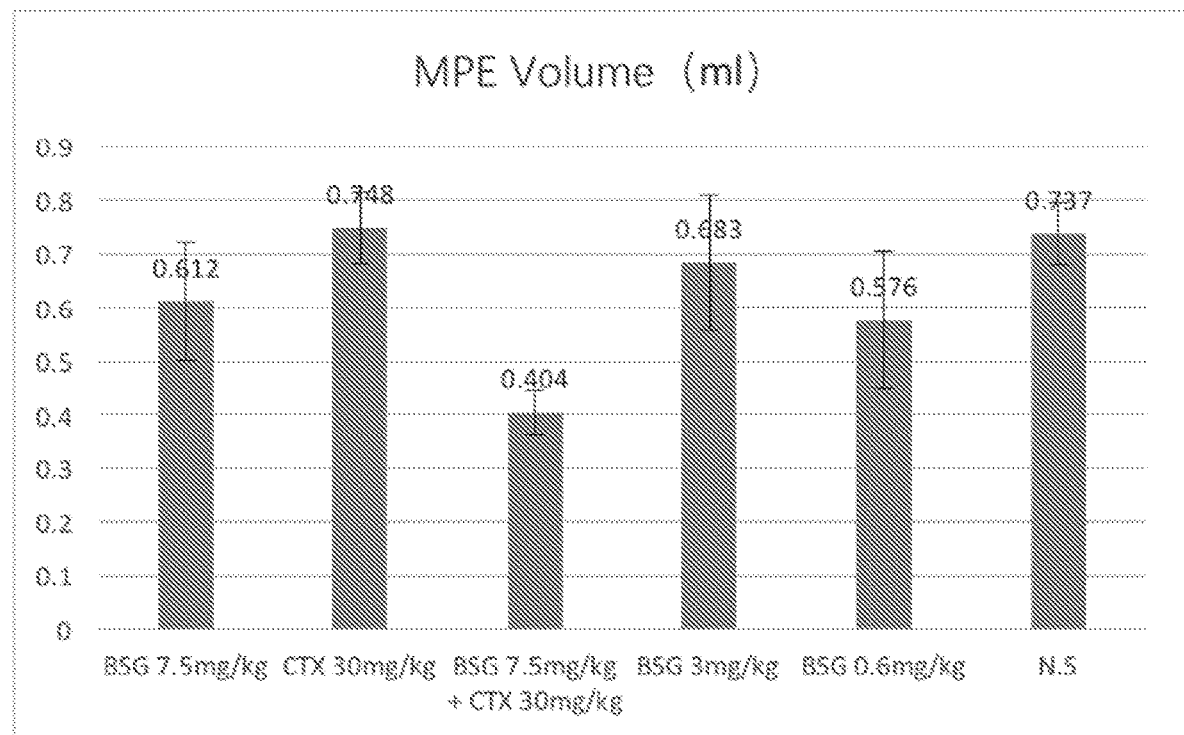
FIG. 3 shows MPE volume for different treatment group on D6 (ml).
Figure 4:
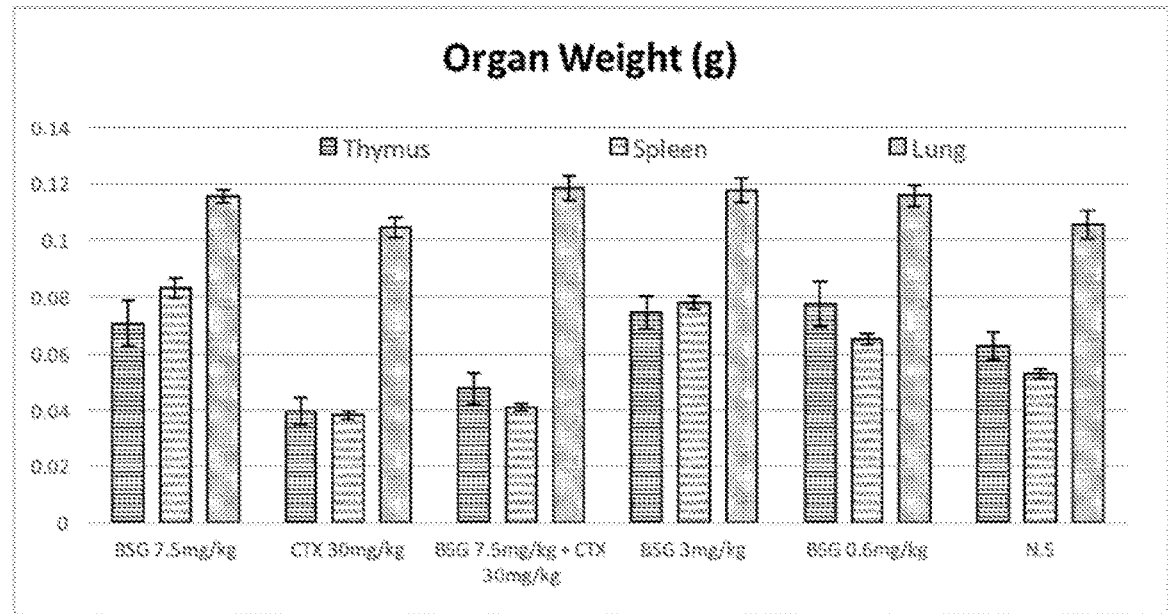
FIG. 4 shows organ toxicity in terms of organ weight post treatment (g).

Results:

1) From the observation on MPE volume, animals in the combined drug Group receiving BSG+CTX had lowest level of MPE, followed by BSG groups. Especially Group A1. BSG 0.6 mg/kg and Group D1. BSG 7.5 mg·kg achieved similar results in controlling MPE (FIG. 3). This indicates that 0.6 mg/kg BSG maybe optimal for the calculation of the human equivalent dose (HED). On the other hand, the lower average weight of organ, such as thymus and spleen of the CTX group of mice suggests excessive toxicity of the drug towards the test animals (FIG. 4).

Figure 5:
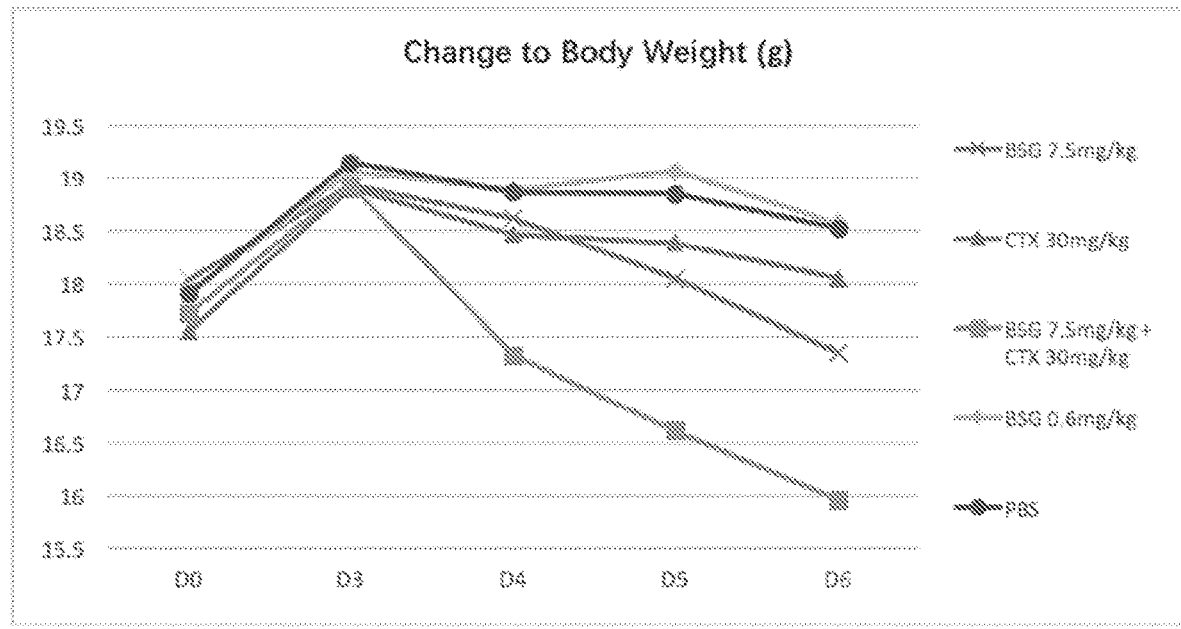
FIG. 5 shows change of mice body weight days post inoculation and treatment (g).

2) The average body weight of mice in BSG 3.0 mg/kg and 0.6 mg/kg groups are similar to those in the control group, indicating low toxicity towards test animals. In contrary, mice in BSG high dose group (7.5 mg/kg), CTX and combine drug usage groups had lower body weight on D7, suggesting toxicity towards test animals (FIG. 5).

3) White blood cell count in peripheral blood suggested level of immune suppression of different drugs and dosage levels. Among these, the suppression is most obvious in BSG+CTX group, while BSG 0.6 mg/kg has lowest level of suppression.

Figure 6:
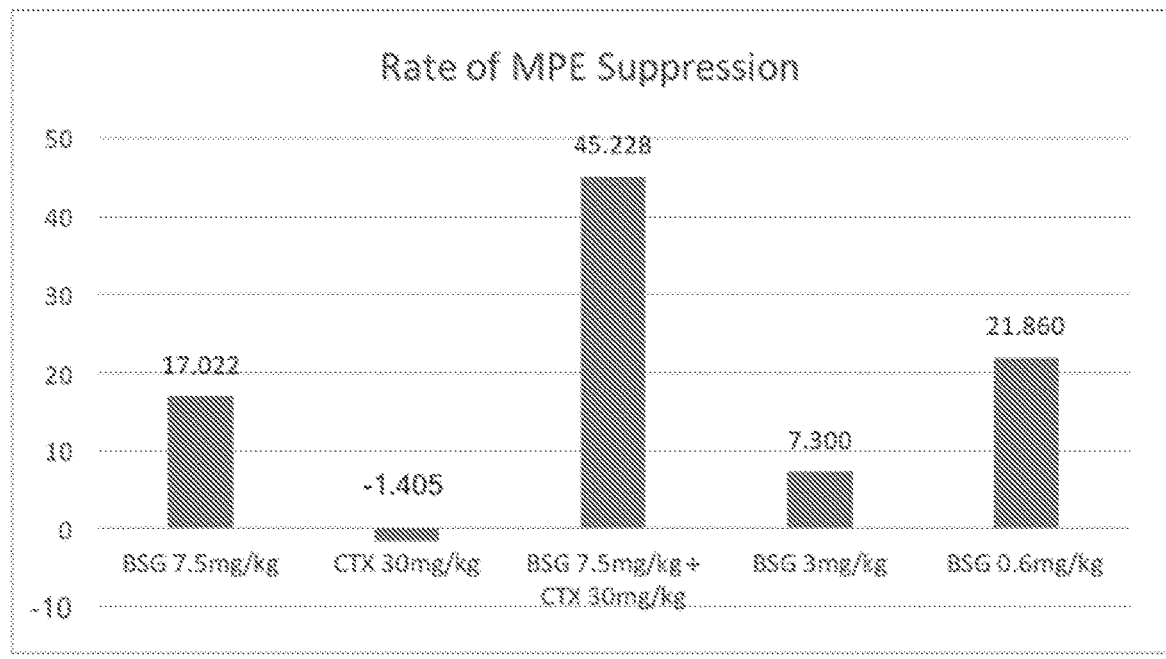
FIG. 6 shows rate of malignant pleural effusion suppression.

4) Based on MPE suppression rate calculation, BSG+CTX had the highest level of suppression, followed by BSG 0.6 mg/kg and 7.5 mg/kg groups (FIG. 6).

5) Table 6 shows the survival status of mice in Groups A2 to E2. Data reflect that the combine drug usage Group C2. BSG+CTX had the best ILS, benefit theoretically from both BSG's MPE suppression effect and CTX's tumor suppression effect. When mice in all other groups die out on D6, 5 mice remain alive in Group C2. In general, BSG groups of mice had better ILS and survival status than mice in CTX and control groups.

TABLE 6

| | No. of Mice | | | | | | | | Ave. Survival | |
|---|---|---|---|---|---|---|---|---|---|---|
| Groups | D 0 | D 3 | D 4 | D 5 | D 6 | D 7 | D 8 | D 9 | (days) | ILS |
| BSG 7.5 mg/kg | 6 | 6 | 6 | 6 | 3 | 1 | 0 | 0 | 6.67 | 14.29 |
| CTX 30 mg/kg | 6 | 6 | 6 | 4 | 1 | 1 | 0 | 0 | 6.00 | 2.86 |
| BSG 7.5 mg/kg + CTX 30 mg/kg | 6 | 6 | 6 | 6 | 6 | 5 | 4 | 1 | 7.67 | 31.43 |
| BSG 0.6 mg/kg | 6 | 6 | 6 | 6 | 2 | 0 | 0 | 0 | 6.33 | 8.57 |
| PBS | 6 | 6 | 6 | 5 | 0 | 0 | 0 | 0 | 5.83 | 0.00 |

Example 4

Concomitant Use of BSG with Chemotherapeutic Drugs in Controlling S180 Cell Line Induced MA Materials: S180 cell line (purchased from CCTCC), female BAL/c mice (6-7 weeks old purchased from Centre of Laboratory Animal for Medical Science, Guangdong), BSG (2 mg/ml, produced in house), DDP (cisplatin, 5 mg/ml, from Jingasu Hansoh Pharma, batch no. 160603), CTX (cyclophosphamide), Sodium Chloride for Injection (2.25 g, 250 ml, 0.9%, from Zhejiang Tianrui, pharmaceutica, batch no. 116102506).

Methods:

1. MA induction and propagation in mice: take logarithmic growth phase cells, adjust cell density to $5\times10^6$/ml, inject mice (i.p., 0.4 ml per animal). Collect MA fluid from mice 7-8 days post inoculation, adjust cell density to $2\times10^7$/ml and inject another 4 mice (i.p., 0.4 ml per animal). Collect MA fluid again from mice 6-7 days post inoculation, adjust cell density to $5\times10^6$/ml and inoculate $2\times10^6$ cells to 48 mice before grouping.

2. Grouping: randomly divide mice 4 d post-inoculation according to body weight into A, B, C, D, E, F groups with 8 mice per group. Treat mice with A. BSG (7.5 mg/kg), B. CTX (50 mg/kg), C. DDP (0.5 mg/kg), D. BSG (7.5 mg/kg)+CTX (50 mg/kg), E. BSG (7.5 mg/kg)+DDP (0.5 mg/kg), F. N.S control for 7 days (Grouping detail see Table 7).

TABLE 7

| Groups | Drug 1 | | | Drug 2 | | |
|---|---|---|---|---|---|---|
| | Name | Dose per mouse | Volume | Name | Dose per mouse | Volume |
| A | BSG i.m | 150 ug | 100 ul | — | — | — |
| B | CTX i.m | 1 mg | 100 ul | — | — | — |
| C | DDP i.p | 10 ug | 100 ul | — | — | — |
| D | BSG i.m | 150 ug | 100 ul | CTX | 1 mg | 100 ul |
| E | BSG i.m | 150 ug | 100 ul | DDP | 10 ug | 100 ul |
| F | BSG i.m | 0 | 100 ul | — | — | — |

3. Observations: 1) record mice behavior and skin/fur glossiness daily, measure body weights and abdominal girth every two days; 2) 2 d post-treatment (D12), obtain blood from eye venous plexus and separate serum for while blood cell count (at least 20 ul). After obtaining blood, execute mice by cervical dislocation, measure pleural fluid volume and record color of fluid; 3) calculate rate of MPE suppression (%)=(1–ave. MPE volume of treatment groups/ave. MA volume of control group)×100%.

Figure 7:
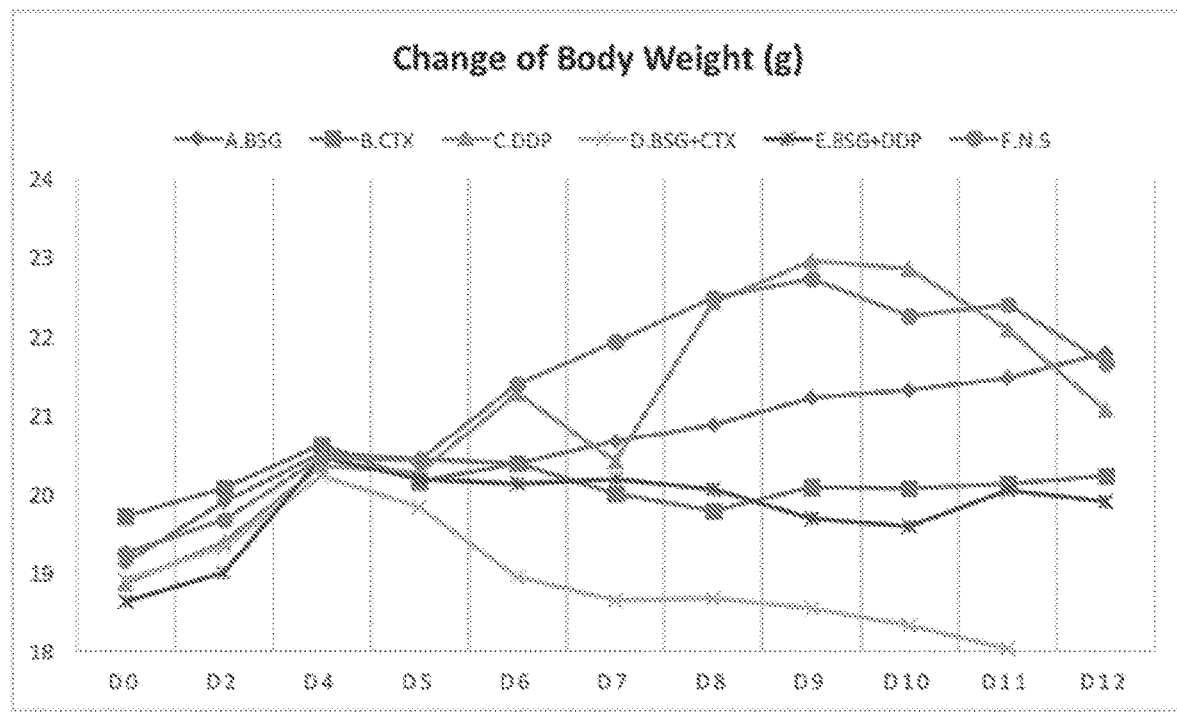
FIG. 7 shows change of body weight days post inoculation and treatment (g).

Results:

1) Except 4 mice in Group C and 1 each in Group D and F, all of the rest of mice were alive until D12. Among the survived mice, DDP and control groups of mice has largest tumor burden and MA volume resulting in higher body weight on D12 compare to other groups (FIG. 7).

2) For the MA color recorded, A. BSG group of mice are mostly faintly red with one mouse having wheat color; B. CTX group has 3 mice with bloody ascites, 4 faintly red and 1 milky color; the 4 surviving mice in C. DDP group are having bloody ascites with one mouse having milky color; in D. BSG+CTX group, the surviving mice all have bloody ascites; for E. BSG+CTX group of mice color are mostly faintly red or milky; while all the surviving mice had bloody ascites for control group F.

Figure 8:
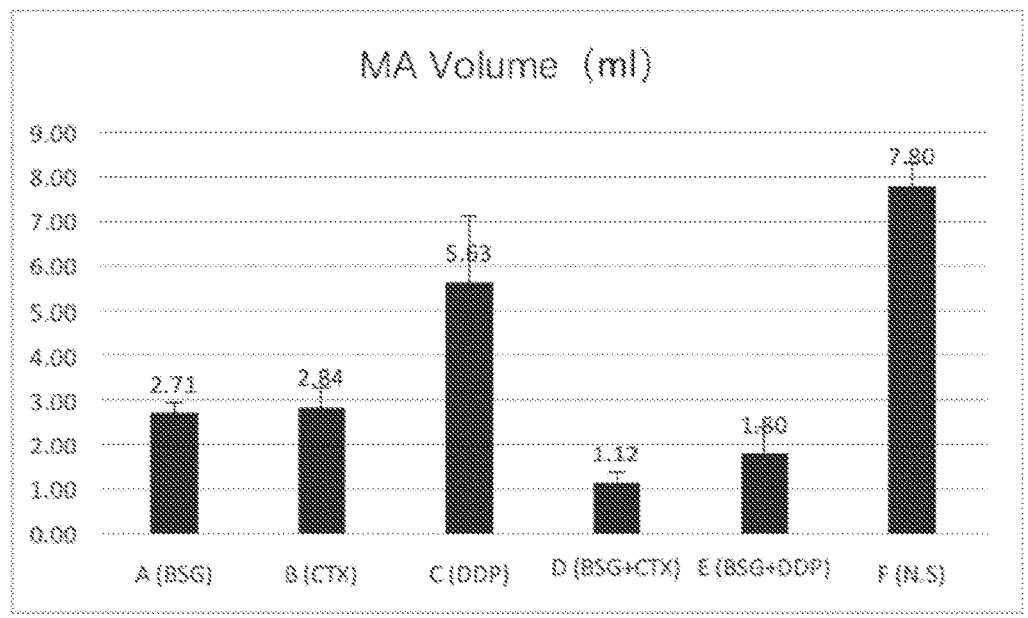
FIG. 8 shows average malignant ascites volume (ml) on D12.
Figure 9:
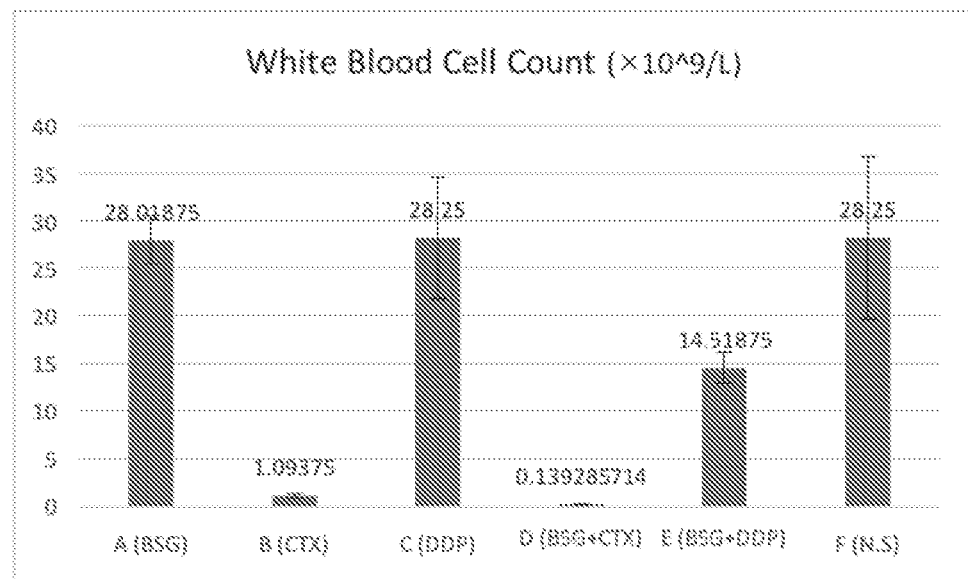
FIG. 9 shows white blood cell count in peripheral blood ($\times 10^9$/L).
Figure 10:
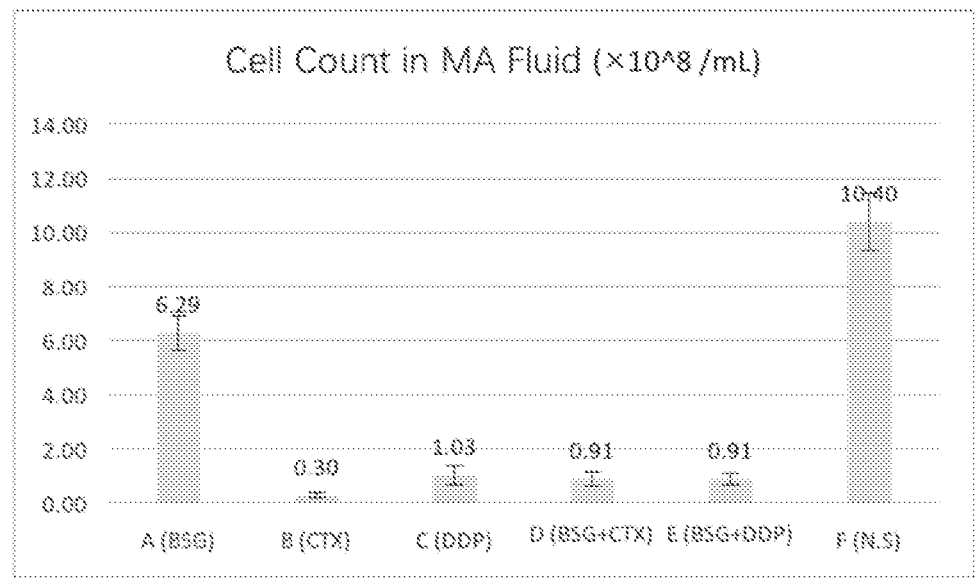
FIG. 10 shows cancerous cells count in malignant ascites fluid ($10^8$/ml).
Figure 11:
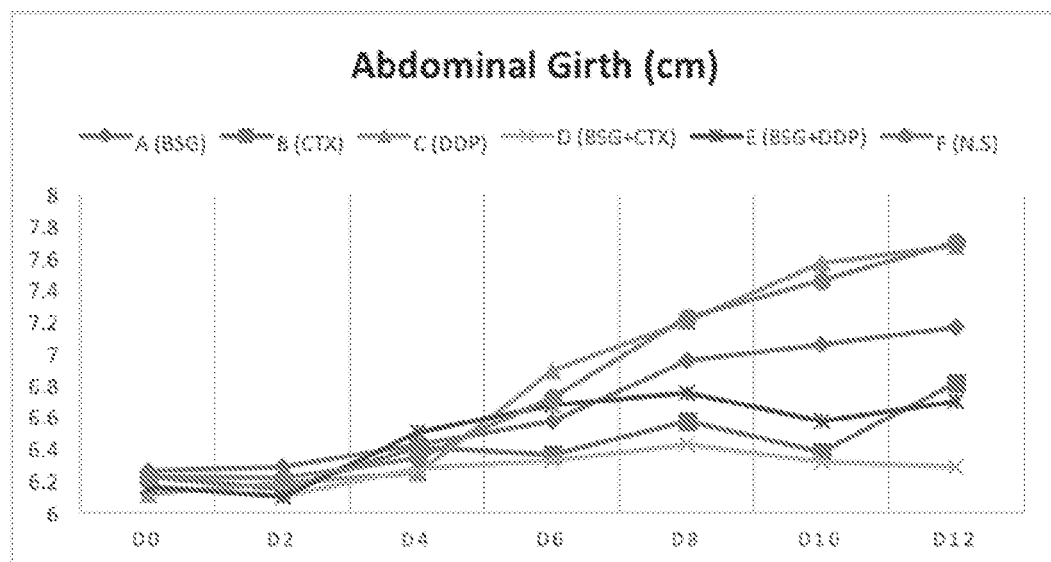
FIG. 11 shows abdominal girth of test animal post inoculation and treatment (cm).

The ascites volume, white blood cell count (WBC) and cancerous cell count in MA is presented in FIG. 8-10. Among the treatment groups, Group D receiving BSG+CTX had best treatment effect with lowest ascites volume. Similarly, this group of mice had lowest WBC count, followed by BSG group. In terms of cancerous cell count in MA, BSG groups of mice actually has higher cancerous cell density, indicating the MA control effect achieved by BSG does not come from suppression of tumorous growth. On the other hand, the rationale of MA control for DDP and CTX was to treat the underlining tumor. FIG. 11 presents the average abdominal girth of testing animal in different treatment groups. From D6 and onwards, mice in the combined treatment groups BSG+CTX and BSG+DDP had smallest abdominal girth, indicating best ascites control.

3) The ascites suppression rates of different treatment groups are presented in Table 9. In accord with the average girth data, combined treatment groups had the best ascites control effect among the groups, followed by the BSG group when used alone. In contrary, DDP did very poor in ascites control.

TABLE 9

| Groups | Ascites Vol.(mL) | SD | SE | MA Suppression |
|---|---|---|---|---|
| A. BSG | 2.71 | 0.66 | 0.23 | 65.2% |
| B. CTX | 2.84 | 1.23 | 0.44 | 63.5% |
| C. DDP | 5.63 | 2.99 | 1.49 | 27.9% |
| D. BSG + CTX | 1.12 | 0.68 | 0.28 | 85.7% |
| E. BSG + DDP | 1.80 | 1.68 | 0.60 | 76.9% |
| F. N.S | 7.80 | 1.31 | 0.53 | 0.0% |

In conclusion, combined usage of BSG and BSG when used alone can achieve better outcome in MA control in comparison to the comparator and control groups.

Example 5

Treatment of Gastric Cancer Patient with BSG

Female subject, 80 years old, was recruited for treatment as regular treatment, i.e. surgery, chemo- and radiotherapy, were deemed unsuitable. Subject received surgical resection of gastric cancer 2 years ago with confirmed lymph node metastasis during surgery. Not surprisingly subject developed recurrent gastric cancer with confirmed liver and lung metastasis. Later, subject developed serious MPE that led to dyspnea, reduced appetite and confinement in bed. There could be 500 ml to 1 L of bloody pleural fluid been extracted daily or every two days.

After patient consent, BSG treatment (s.c., 2000 mg every two days, continuous till this report for about 3 months) was initiated to treat underlining cancer with hope to restore patient's own immunity and delay cancer progression. On day 14, patient started to experience fluid reduction and the color of fluid extracted fade gradually. After the 9th dose (18 days post treatment), there is obvious relief of MPE, increase mobility and return of appetite. On 22th day, ultrasound examination showed complete remission of MPE. Subject is under continuous treatment without obvious toxicity.

Example 6

Treatment of Breast Cancer Patient with BSG

Female subject, 54 years old was recruited for treatment due to recurrent breast cancer (ductal carcinoma with confirmed lung metastasis). Subject recently developed MPE. BSG treatment (s.c., 1000 mg every three days) was given for underlining cancer. By the end of second week post treatment, patient start to experience relief of MPE, with reduced volume of bloody pleural fluidextract and fade in color. After the 7th dose (21 days post treatment), there was complete remission of MPE with increase mobility.

REFERENCES

Antony V B, Loddenkemper R, Astoul P, et al. Management of malignant pleural effusions. Eur Respir J 2001; 18: 402-19.

Antunes G, Neville E, Duffy J, Ali N: BTS guidelines for the management of malignant pleural effusions. *Thorax* 2003; 58: ii29-ii38.

Barni S, et al., A novel perspective for an orphan problem: Old and new drugs for the medical management of malignant ascites. Critical Reviews in Oncology/Hematology 79 (2011) 144-153.

Dawei Chen, and Jinming Yu, et al. Sustained response of malignant pericardial effusion to intrapericardial bevacizumab in an advanced lung cancer patient: a case report and literature review. OncoTargets and Therapy. 2015.

Kaifi J T, Toth J W, Gusani N J, et al. Multidisciplinary management of malignant pleural effusion. Journal Surg Oncol 2012; 105: 731-8.

Light R W, Lee Y C G. Textbook of pleural diseases. Philadelphia: Lippincott, Williams and Wilkins; 2001. 4.

Lila Ammouri and Eric E Prommer. Palliative treatment of malignant ascites: profile of catumaxomab. Biologics. 2010; 4: 103-110.

Magda Spella, Anastasios D. Giannou, Georgios T. Stathopoulos (2015) Switching off malignant pleural effusion formation—fantasy or future? J Thorac Dis 2015; 7(6): 1009-1020.

Michael Ried, Hans-Stefan Hofmann. The Treatment of Pleural Carcinosis With Malignant Pleural Effusion. Dtsch Arztebl Int 2013; 110(18).

Muhammad W. Saif, Imran A. P. Siddiqui, and Muhammad A. Sohail. Management of ascites due to gastrointestinal malignancy. Ann Saudi Med. 2009 September-October; 29(5): 369-377.

Neragi-Miandoab S: Malignant pleural effusion, current and evolving approaches for its diagnosis and management. Lung Cancer 2006; 54: 1-9.

Olopade O I and Ultmann J E, Malignant effusions. *CA: A Cancer Journal for Clinicians* 1991; Vol. 41, No. 3; 166-179.

Putnam J B: Malignant pleural effusions. Surg Clin North Am 2002; 82: 867-83.

Schulze M, et al., Effective Treatment of Malignant Pleural Effusion by Minimal Invasive Thoracic Surgery: Thoracoscopic Talc Pleurodesis and Pleuroperitoneal Shunts in 101 Patients *Ann Thorac Surg* 2001; 71: 1809-12.

Stathopoulos G T, Kalomenidis I. Malignant pleural effusion: tumor-host interactions unleashed. Am J Respir Crit Care Med 2012; 186:487-92.

Warren W H, et al., Identification of clinical factors predicting Pleurx® catheter removal in patients treated for malignant pleural effusion. *European Journal of Cardiothoracic Surgery* 2008; 33: 89-94.

Warren W H, et al., Management of malignant pleural effusions using the Pleur(x) catheter. Ann Thorac Surg 2008; 85:1049-55.

The invention claimed is:

1. A method of treating malignant effusion in a subject, wherein the method comprises administering to the subject a therapeutically effective amount of a pharmaceutical composition comprising polyinosinic:polycytidylic acid (PIC), an aminoglycoside, and calcium chloride ($CaCl_2$),
    wherein the malignant effusion is selected from malignant pleural effusion, or malignant ascites.

2. The method of claim 1, wherein the aminoglycoside is selected from the group consisting of Dihydrostreptomycin, Mannosidostreptomycin, Amikacin, Butyrosin, Debekacin, Destomycin, Gentamicin, Kanamycin, Lividomycin, Netilmicin, Neomycin, Paromomycin, Ribostamycin, Sisomicin, Streptomycin, Streptothricin, Tobramycin and Validamycin.

3. The method of claim 1, wherein the aminoglycoside is Kanamycin.

4. The method of claim 1, wherein the PIC is a polyriboinosinic-polyribocytidylic acid.

5. The method of claim 1, wherein the pharmaceutical composition further comprises a pharmaceutically acceptable vector, adjuvant, excipient, or diluent.

6. The method of claim 1, wherein the pharmaceutical composition further comprises an antigen selected from a tumor antigen, cancer neoantigen, plant antigen, animal antigen, microbial antigen, or viral antigen.

7. The method of claim 1, wherein the pharmaceutical composition is administered to the subject by parenteral administration, intramuscular injection, intraperitoneal perfusion, intrapleural perfusion, intravenous perfusion, subcutaneous injection, intrapericardial injection, inhalation, endorectral perfusion, suppository, intra nasal, ophthalmic, transdermal or oral administration.

8. The method of claim 1, wherein the malignant effusion arises from a primary tumor originating in lung, lymph, liver, stomach, colon, breast, ovary, pancreas, biliary duct, esophagus, brain, nose or prostrate gland.

9. The method of claim 1, wherein the malignant effusion is located in the pleural cavity and arises from the metastases of lung cancer, lymphoma, stomach cancer, colon cancer, breast cancer or ovary cancer.

10. The method of claim 1, wherein the malignant effusion is located in the peritoneal cavity and arises from the metastases of the ovary cancer, pancreatic cancer, biliary duct cancer, or esophagus cancer.

11. The method of claim 1, wherein the pharmaceutical composition comprises:
    a) PIC in an amount of 0.1 to 10.0 g/L;
    b) kanamycin in an amount of 100 to 5000 IU per 1.0 mg of PIC; and
    c) calcium chloride in an amount of 0.2 to 4.0 mmol/L.

12. The method of claim 1, wherein the pharmaceutical composition is administered during and/or via a chest drainage, thoracentesis, temporary or permanent pleural catheter insertion, thoracoscopic pleurodesis, pericardial intraluminal stenting or fenestrated drainage, or surgical shunting procedure.

* * * * *